(12) United States Patent
El-Rashidy et al.

(10) Patent No.: US 6,193,992 B1
(45) Date of Patent: Feb. 27, 2001

(54) FEMALE SEXUAL DYSFUNCTION TREATMENT

(75) Inventors: Ragab El-Rashidy, Deerfield; Bruce Ronsen, River Forest, both of IL (US)

(73) Assignee: Pentech Pharmaceuticals, Inc., Buffalo Grove, IL (US)

(*) Notice: Subject to any disclaimer, the term of this patent is extended or adjusted under 35 U.S.C. 154(b) by 0 days.

(21) Appl. No.: 09/345,009

(22) Filed: Jul. 2, 1999

Related U.S. Application Data

(63) Continuation-in-part of application No. 09/016,252, filed on Jan. 30, 1998, now Pat. No. 5,945,117.

(51) Int. Cl.$^7$ .............................. A61F 6/06; A61L 15/16
(52) U.S. Cl. ................................ 424/430; 424/447
(58) Field of Search ........................... 424/430, 447, 424/448

(56) References Cited

U.S. PATENT DOCUMENTS 5,562,917 * 10/1996 Durif et al. ...................... 424/447
5,945,117 * 8/1999 El-Rashidy et al. .............. 424/430

* cited by examiner

Primary Examiner—Thurman K. Page
Assistant Examiner—S. Howard
(74) Attorney, Agent, or Firm—Olson & Hierl, Ltd.

(57) ABSTRACT

Sexual dysfunction in human females can be ameliorated, without substantial undesirable side effects, by apomorphine. Administration of apomorphine increases nerve stimulated clitoral intracavernosal blood flow and vaginal wall blood flow for enhanced clitoral erection and vaginal engorgement in a female. A plasma concentration of apomorphine of no more than about 5.5 nanograms per milliliter is preferably maintained.

18 Claims, 3 Drawing Sheets

FEMALE SEXUAL DYSFUNCTION TREATMENT

CROSS-REFERENCE TO RELATED APPLICATION

This application is a continuation-in-part of U.S. Ser. No. 09/016,252, filed on Jan. 30, 1998, now U.S. Pat. No. 5,945,117.

FIELD OF THE INVENTION

This invention relates to methods for ameliorating female sexual dysfunction.

BACKGROUND OF THE INVENTION

Apomorphine is a dopamine receptor agonist that has been widely utilized as an emetic agent, sedative, antiparkinsonian agent as well as a behavior altering agent. Recent research and clinical studies have demonstrated that in males apomorphine has an erectogenic effect manifested by penile erection.

The effect of apomorphine on female sexual functionality has not been previously investigated. Females also can have sexual dysfunction, however, that increases with age. Female sexual dysfunction usually is associated with the presence of vascular risk factors, genital smooth muscle atrophy, and onset of menopause. Some of the vascular and muscular mechanisms that contribute to penile erection in the male are believed to be similar vasculogenic factors in female genital response. It is known that in women sexual arousal is accompanied by arterial inflow which engorges the vagina and increases vaginal lubrication, and that the muscles in the perineum assist in achieving clitoral erection.

In the female patient, sexual dysfunction can arise from organic and psychogenic causes, or from a combination of the foregoing. Female sexual dysfunction includes a failure to attain or maintain vaginal lubrication-swelling responses of sexual excitement until completion of the sexual activity. Organic female sexual dysfunction is known to be related in part to vasculogenic impairment resulting in inadequate blood flow, vaginal engorgement insufficiency and clitoral erection insufficiency.

Female sexual dysfunction has not been studied as extensively as male sexual dysfunction. This has partly been due to historical belief that female sexual dysfunction was orgasmic-related (delayed or non-orgasmic) or libido, and hence lacked an appropriate animal model.

The use of New Zealand White male rabbits as animal models for impotence has been well established. More recently, studies have reported that New Zealand White female rabbits are also suitable animal model for studying the vascular pathology in female sexual dysfunction. Such studies have shown that vaginal vascular engorgement and clitoral erection depend on blood inflow. See, for example, Park et al, "Vasculogenic female sexual dysfunction: the hemodynamic basis for vaginal engorgement insufficiency and clitoral erectile insufficiency," *International Journal of Impotence Research*, 9, (1), 27–37 (March 1997).

For psychogenic sexual dysfunction management, psychological sex therapy can also be employed to help the patient.

Apomorphine previously was shown to have very poor oral bioavailability. See, for example, Baldessarini et al., in Gessa et al., (eds.), *Apomorphine and Other Dopaminomimetics, Basic Pharmacology*, 1, 219–228, Raven Press, N.Y. (1981).

More recently, studies with males show that oral administration of apomorphine can be used to induce an erection in a psychogenic male patient, as long as the apomorphine dose required to achieve a significant erectile response is not accompanied by nausea and vomiting or other serious undesirable side effects such as arterial hypotension, flushing and diaphoresis. See U.S. Pat. No. 5,624,677 to El-Rashidy et al. and Heaton et al., *Urology*, 45, 200–206 (1995). The specific mechanisms by which apomorphine acts to produce an erectile response in a human patient are not yet completely understood but are believed to be centrally acting through dopamine receptor stimulation in the medial preoptic area of the brain.

It has now been found that certain controlled delivery systems for apomorphine can provide a practical therapeutic use in ameliorating sexual dysfunction in human females while reducing the likelihood of undesirable side effects.

SUMMARY OF THE INVENTION

Administration of apomorphine to a human female increases nerve stimulated clitoral intracavernosal blood flow and vaginal wall blood flow, each of which is associated respectively with enhanced clitoral erection and vaginal engorgement in a female.

A sublingual apomorphine dosage form, usually containing about 2 to about 12 milligrams, preferably about 2 to about 8 milligrams, of apomorphine, is preferred for producing sexual readiness in human females without inducing substantial nausea or other undesirable side effects. Other dosage forms can be utilized as well.

Administration of apomorphine in an amount sufficient to produce vaginal engorgement is effected preferably about 15 to about 20 minutes prior to sexual activity. The plasma concentration of apomorphine is maintained at no more than about 5.5 nanograms per milliliter, preferably about 0.3 to about 4 nanograms per milliliter, and more preferably about 1 to about 2 nanograms per milliliter, so as to maintain a circulating serum level and mid-brain tissue level of apomorphine during the period of sexual activity sufficient to maintain vaginal engorgement, its associated lubrication and clitoral erection during coitus, but less than the amount that induces substantial nausea.

While sublingual administration of apomorphine is preferred for present purposes, other routes of administration are also suitable. Illustrative of such alternate routes of administration are buccal patch, transdermal patch, cream, ointment, intranasal spray, tablets, capsules and the like.

DETAILED DESCRIPTION OF PREFERRED EMBODIMENTS

Figure 1:
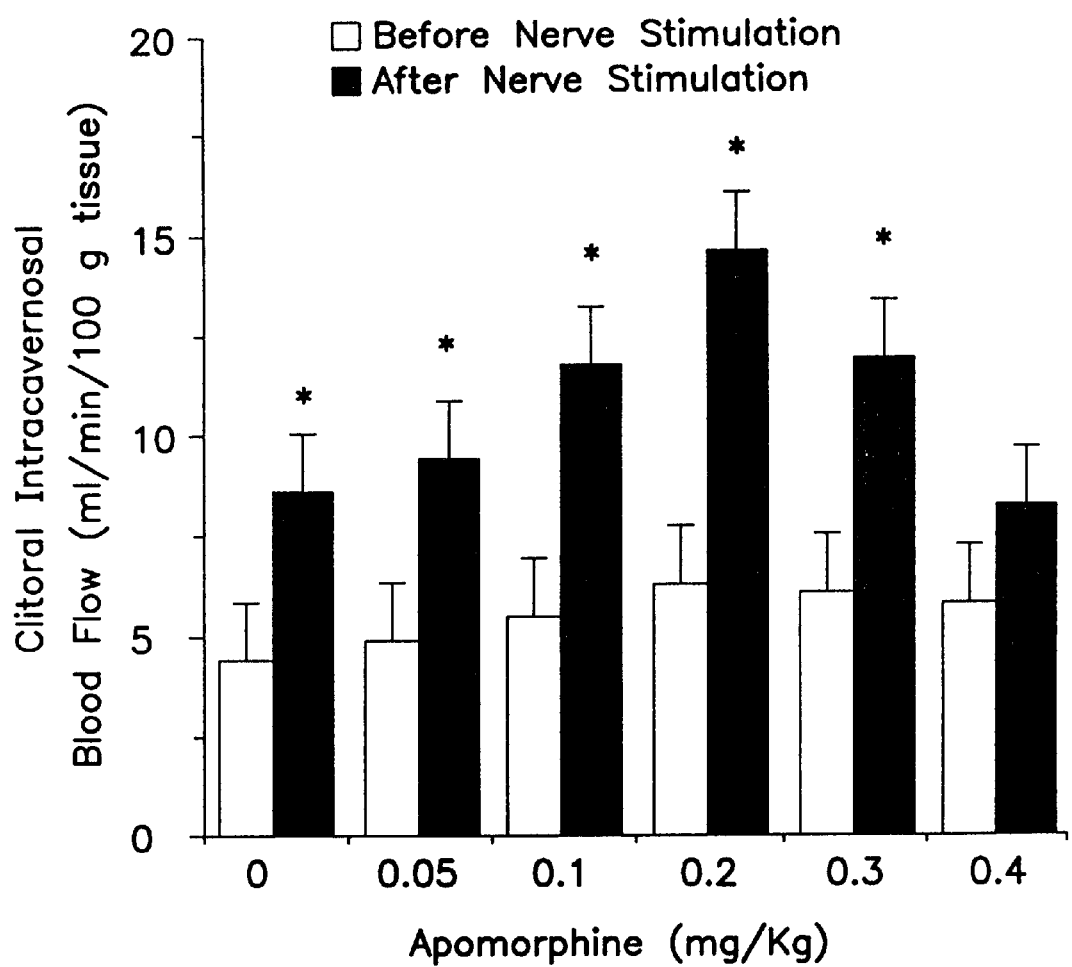
FIG. 1 is a bar graph depicting the effect of apomorphine on female rabbit clitoral blood flow in milliliters per minute per 100 grams tissue before and after nerve stimulation for placebo and intravenous apomorphine amounts of 0.05, 0.1, 0.2, 0.3 and 0.4 milligrams per kilogram body weight.

Apomorphine can be represented by the following formula

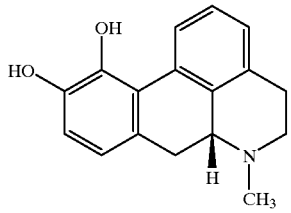

and exists in a free base form or as an acid addition salt. For the purposes of the present invention apomorphine hydrochloride is preferred; however, other pharmacologically acceptable moieties thereof can be utilized as well. The term "apomorphine" as used herein includes the free base form of this compound as well as the pharmacologically acceptable acid addition salts thereof. In addition to the hydrochloride salt, other acceptable acid addition salts are the hydrobromide, the hydroiodide, the bisulfate, the phosphate, the acid phosphate, the lactate, the citrate, the tartrate, the salicylate, the succinate, the maleate, the gluconate, and the like.

Apomorphine is a dopamine receptor agonist that has been recognized also as an emetic when administered subcutaneously in about a 5-milligram dose. For the purposes of the present invention, apomorphine is administered in an amount sufficient to excite cells in the mid-brain region of the patient but with minimal side effects. This cell excitation is believed to be part of a cascade of stimulation that is likely to include neurotransmission with serotonin and oxytocin.

It is known from studies with males that the dopamine receptors in the mid-brain region of a male patient can be stimulated to a degree sufficient to cause an erection by the sublingual administration of apomorphine so as to maintain a plasma concentration of apomorphine of no more than about 5.5 nanograms per milliliter (5.5 ng/ml).

The pharmacokinetics of apomorphine are the same for both females and males, based on apomorphine hydrochloride studies with humans (Parkinson's disease) and animals reported in the literature. Thus, the onset and duration of effect from a given dose of apomorphine in men compared to animals applies to human females as well.

It was found that an intravenous dosage of apomorphine of about 100 micrograms per kilogram ($\mu$g/kg) of body weight was optimum for producing a vasculogenic effect on nerve stimulated vaginal and clitoral blood flow in female rabbit studies. For human females, this dosage correlates to an optimum dosage of about 1/10 or 10 $\mu$g/kg of body weight. In sublingual tablet forms, the bioavailability of apomorphine is about 13% compared to subcutaneously administered apomorphine hydrochloride. Assuming an average female body weight of about 70 kilograms, a significant sexual readiness dose of apomorphine is about 76 $\mu$g/kg or about a 5.3 milligram (mg) per tablet. A dosage range of about 2 mg to about 12 mg, therefore, produces sexual readiness (i.e., clitoral erectogenesis and vaginal engorgement on sexual stimulation) in women.

Sublingual administration preferably takes place over a time period in the range of about 2 to about 10 minutes, or longer, more preferably about 15 to about 20 minutes, prior to sexual activity. The amount of apomorphine administered sublingually to a human female over this time period preferably is in the range of about 25 $\mu$g/kg of body weight to about 80 $\mu$g/kg of body weight.

Illustrative preferred sublingual dosage forms are set forth in Table I, below.

TABLE I

150 Milligram Apomorphine Hydrochloride Sublingual Tablets

| 3-mg Tablet | |
|---|---|
| Apomorphine Hydrochloride | 2.00 wt-% |
| Mannitol | 66.67 wt-% |
| Ascorbic Acid | 3.33 wt-% |
| Citric Acid | 2.00 wt-% |
| Avicel PH102[1] | 15.00 wt-% |
| Methocel E4M[2] | 10.00 wt-% |
| Aspartame | 0.67 wt-% |
| Magnesium Stearate | 0.33 wt-% |
| 4-mg Tablet | |
| Apomorphine Hydrochloride | 2.66 wt-% |
| Mannitol | 66.00 wt-% |
| Ascorbic Acid | 3.33 wt-% |
| Citric Acid | 2.00 wt-% |
| Avicel PH102[1] | 15.00 wt-% |
| Methocel E4M[2] | 10.00 wt-% |
| Aspartame | 0.67 wt-% |
| Magnesium Stearate | 0.33 wt-% |
| 5-mg Tablet | |
| Apomorphine Hydrochloride | 3.33 wt-% |
| Mannitol | 65.34 wt-% |
| Ascorbic Acid | 3.33 wt-% |
| Citric Acid | 2.00 wt-% |
| Avicel PH102[1] | 15.00 wt-% |
| Methocel E4M[2] | 10.00 wt-% |
| Aspartame | 0.67 wt-% |
| Magnesium Stearate | 0.33 wt-% |

[1]microcrystalline cellulose
[2]hydroxypropylmethyl cellulose

If desired, and in order to facilitate absorption and thus bioavailability, the presently contemplated dosage forms can also contain, in addition to tabletting excipients, a $\beta$-cyclodextrin or a $\beta$-cyclodextrin derivative such as hydroxypropyl-$\beta$-cyclodextrin (HPBCD). Illustrative dosage forms containing HPBCD are shown in Tables II and III, below.

TABLE II

Apomorphine Hydrochloride Sublingual Tablets With Hydroxypropyl-$\beta$-Cyclodextrin

| | mg/Tab |
|---|---|
| Apomorphine Hydrochloride | 4.0 |
| HPBCD | 5.0 |
| Ascorbic Acid | 10.0 |
| PEG8000 | 39.5 |
| Mannitol | 39.5 |
| Aspartame | 2.0 |
| TOTAL | 100.0 |

TABLE III

Apomorphine Hydrochloride Sublingual Tablets With $\beta$-Cyclodextrin

| | mg/Tab |
|---|---|
| Apomorphine Hydrochloride | 5.0 |
| $\beta$-Cyclodextrin | 20.0 |

TABLE III-continued

Apomorphine Hydrochloride Sublingual
Tablets With β-Cyclodextrin

|  | mg/Tab |
|---|---|
| Ascorbic Acid | 5.0 |
| Mannitol | 68.9 |
| Magnesium Stearate | 1.0 |
| D&C Yellow 10 Aluminum Lake | 0.1 |
| TOTAL | 100.0 |

Additional sublingual apomorphine dosage forms are illustrated in Table IV, below. The amounts of apomorphine are expressed as apomorphine hydrochloride hemihydrate.

TABLE IV

Sublingual Apomorphine Tablets

|  | Amount per Tablet (mg) |
|---|---|
| Apomorphine-HCl, USP | 2, 4, 6 or 8 |
| Mannitol, USP | QS |
| Avicel PH 102 NF[1] | 22.7 |
| HPMC 2910, Type E4M Premium, USP/NF[2] | 5.0 |
| Citric Acid, Anhydrous, USP | 2.0 |
| Ascorbic Acid, USP/NF | 3.0 |
| Magnesium Stearate, NF | 1.2 |
| Color Agent | 1.2 |
| Sweetener | 1.0 |
| Total Tablet Weight, mg | 60.0 |
| Apomorphine-HCl, USP | 2, 3, 4, 5, or 6 |
| Mannitol, USP | QS |
| Avicel PH 102 NF[1] | 20.0 |
| HPMC 2910, Type E4M Premium, USP/NF[2] | 10.0 |
| Citric Acid, Anhydrous, USP | 3.5 |
| Ascorbic Acid, USP/NF | 0.2 |
| Edetate Disodium Dihydrate, USP/NF | 0.1 |
| Colloidal Silicon Dioxide, NF | 0.1 |
| Magnesium Stearate, NF | 1.5 |
| Color Agent | 2.0 |
| Flavoring | 2.0 |
| Sweetener | 2.0 |
| Total Tablet Weight, mg | 100.0 |

[1]microcrystalline cellulose
[2]hydroxypropylmethyl cellulose

The onset of nausea can be obviated or delayed by delivering apomorphine at a controlled dissolution rate so as to provide circulating serum levels and mid-brain tissue levels of apomorphine sufficient for vaginal and clitoral engorgement without inducing nausea. When apomorphine is administered at or near the relatively higher amounts of the aforementioned dosage range, the likelihood of nausea onset can be reduced by concurrent administration of a ganglionic agent (inhibitor of ganglionic response) such as nicotine or lobeline sulfate. For this purpose, the weight ratio of apomorphine to ganglionic agent is in the range of about 10 to about 1.

Other antiemetic agents that can be used in conjunction with apomorphine are antidopaminergic agents such as metoclopramide, and the phenothiazines, e.g., chlorpromazine, prochlorperazine, pipamazine, thiethylperazine, oxypendyl hydrochloride, and the like. Also suitable are the serotonin (5-hydroxytryptamine or 5-HT) antagonists such as domperidone, odansetron (commercially available as the hydrochloride salt under the designation Zofran®), and the like, the histamine antagonists such as buclizine hydrochloride, cyclizine hydrochloride, dimenhydrinate (Dramamine), and the like, the parasympathetic depressants such as scopolamine, and the like, as well as other anti-emetics such as metopimazine, trimethobenzamide, benzquinamine hydrochloride, diphenidol hydrochloride, and the like.

Nicotine-containing dosage forms and domperidone-containing dosage forms are illustrated in Table V, below.

TABLE V

Apomorphine Hydrochloride Sublingual Tablets
Containing an Anti-Emetic Agent

|  | mg/Tab |
|---|---|
| Apomorphine Hydrochloride | 5.0 |
| Ascorbic Acid | 5.0 |
| Mannitol | 67.9 |
| Magnesium Stearate | 1.0 |
| Nicotine | 1.0 |
| β-Cyclodextrin | 20.0 |
| D&C Yellow 10 Aluminum Lake | 0.1 |
| TOTAL | 100.0 |
| Apomorphine Hydrochloride | 5.0 |
| Ascorbic Acid | 5.0 |
| Mannitol | 58.9 |
| Magnesium Stearate | 1.0 |
| Domperidone | 10.0 |
| β-Cyclodextrin | 20.0 |
| D&C Yellow 10 Aluminum Lake | 0.1 |
| TOTAL | 100.0 |

The preferred sublingual dosage forms dissolve within a time period of at least about 2 minutes but preferably less than about 10 minutes. The dissolution time can be longer, however, if desired as long as the necessary plasma concentration of apomorphine can be maintained. More preferably, the dissolution time in water for the presently contemplated dosage forms is about 3 minutes to about 5 minutes.

Controlled slow release sublingual or buccal dosage forms of apomorphine suitable for practicing the present invention are described in U.S. Pat. No. 5,624,677 to El-Rashidy et al. and in U.S. Pat. No. 5,888,534 to El-Rashidy et al.

Suitable transdermal patches and water-soluble gels for the topical administration of apomorphine in practicing the present invention are described in U.S. Pat. No. 5,562,917 to Durif and El-Rashidy.

Gel-forming polymer useful for compounding the apomorphine compositions may be any suitable polymer which is hydrophilic and water-dispersible, has free carboxylic groups, and forms a gel of substantially uniform consistency. Illustrative such polymers are the polysaccharides such as algin, xanthan, guar and the like, and synthetic hydrophilic polymers such as the alkyl celluloses, hydroxyalkyl celluloses, polyvinyl sufonates, polyacrylates, polyacrylamides and the like. Preferred polymers for use in the compositions of the invention are hydroxypropyl methylcellulose and water dispersible polycarboxylated vinyl polymers. Polyacrylic acid polymers are particularly preferred for the present purposes. The molecular weight of the polymer is desirably in the range of about 1,250,000 to about 4,000,000. Suitable polyacrylic acid polymers include, but are not limited to, polyacrylic acid polymers lightly cross-linked with a polyalkenyl polyether such as those commercially available from B.F. Goodrich, Cincinnati, Ohio, under the trademarks Carbopol 934, 940, and 941. Carbopol 934® is a particularly preferred polymer for this purpose.

The polymer is present in an amount sufficient to cause gelling of the composition and impart the desired viscous consistency to the topical formulation. The apomorphine compositions advantageously comprise about 0.1 to about 7% by weight of the polymer, preferably about 0.5% to about 1.5%, and most preferably about 1% by weight of the polymer, based on the total weight of the composition.

Aqueous solutions of these polymers form gels when neutralized with a base. Water-soluble bases which may be used to promote gelling of polymers such as Carbopols™ include inorganic bases such as an aqueous solution of ammonium hydroxide, NaOH, and organic amines, e.g., alkylamines such as methylamine and ethylamine, dialkylamines trialkylamines, alkanolamines, dialkanolamines, and the like.

One preferred dosage form for practicing the present invention utilizes an aqueous gel or cream composition which contains apomorphine and a skin permeation enhancer therefor. Another dosage form utilizes a pressure-sensitive medical grade silicone adhesive matrix which contains apomorphine and a permeation enhancer therefor. Other suitable dosage forms are rectal and vaginal suppositories, buccal patches, tablets, capsules, and the like.

A contemplated skin permeation enhancer is an aromatic or aliphatic carbocyclic compound containing pendant hydroxyl groups, such as butylated hydroxytoluene (BHT), butylated hydroxyanisole (BHA) or a hydroxypropyl-beta-cyclodextrin (HPBCD), and the like, which can be present in amount up to about 30 percent by weight of the gel or the adhesive matrix.

Apomorphine is present in the dosage form for purposes of the present invention in an amount in the range of about 0.1 to about 3 percent by weight of the gel or the adhesive matrix.

Illustrative suitable intranasal spray composition that can be used for practicing the present invention is as follows:

| | |
|---|---|
| Apomorphine-HCl, USP | 4 mg/ml |
| $Na_2S_2O_6$ | 0.05 wt.-% |
| Methyl paraben | 0.1 wt.-% |
| Propyl paraben | 0.02 wt.-% |
| NaCl | 0.8 wt.-% |
| purified water, USP | q.s. |

The following examples further illustrate the vasculogenic effect of apomorphine on vaginal and clitoral blood flow in females, employing an appropriate female animal model.

Methods

New Zealand White female rabbits (n=6, about 3.5–4 kg) were anesthetized with intravenous administration of pentobarbital. A 20 gauge angiocatheter was placed into the right carotid artery for measurement of systemic arterial pressure. A midline abdominal incision was made and the pelvic nerve branch to the vagina and clitoris was dissected. Nerve stimulation was performed with a Harvard subminiature electrode placed around the pelvic nerve branch to the vagina and clitoris and connected to a Grass SD-9 stimulator. Clitoral intracavernosal and vaginal wall blood flow were measured with a laser Doppler flow probe placed directly into the clitoral cavernosal tissue or into the vaginal wall and connected to a laser Doppler flowmeter.

Basal arterial blood pressure and clitoral and vaginal blood flow were each recorded before and then after stimulation of the pelvic nerve branch to the clitoris and vagina. After this, apomorphine was administered through the ear vein in a dose response manner (0.05 mg/kg, 0.1 mg/kg, 0.2 mg/kg, 0.3 mg/kg and 0.4 mg/kg). The effect of apomorphine administration on arterial blood pressure and clitoral and vaginal blood flow were each recorded before and then after nerve stimulation.

Results

1. Effect of apomorphine on clitoral intracavernosal blood flow.

Stimulation of the pelvic nerve branch to the vagina and clitoris caused a significant increase in clitoral intracavernosal blood flow. Intravenous administration of apomorphine did not affect baseline clitoral intracavernosal blood flow. Intravenous administration of apomorphine at concentrations of 0.05 mg/kg to 0.2 mg/kg caused a concentration dependent increase in nerve stimulation-induced peak clitoral intracavernosal blood flow, as depicted graphically in FIG. 1. In particular, apomorphine at 0.1 mg/kg, 0.2 mg/kg and 0.3 mg/kg caused a statistically significant increase in nerve stimulation-induced peak clitoral intracavernosal blood flow compared to that observed before apomorphine administration (FIG. 1).

2. Effect of apomorphine on vaginal wall blood flow.

Figure 2:
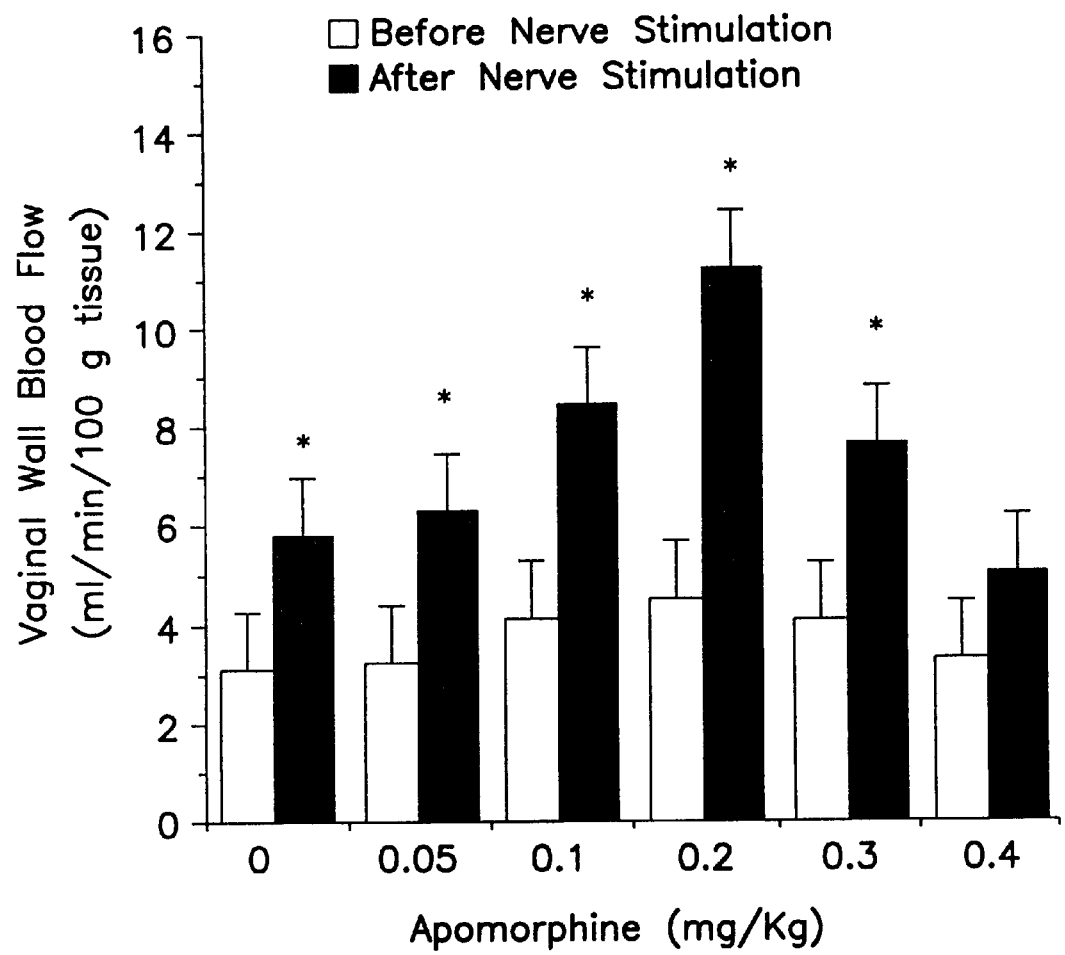
FIG. 2 is a bar graph depicting the effect of apomorphine on female rabbit vaginal wall blood flow in milliliters per minute per 100 grams tissue before and after nerve stimulation for placebo and intravenous apomorphine amounts of 0.05, 0.1, 0.2, 0.3 and 0.4 milligrams per kilogram body weight.

Intravenous administration of apomorphine did not affect basal vaginal wall blood flow. Apomorphine at concentrations of 0.05 and 0.2 mg/kg caused a concentration dependent increase in nerve stimulation-induced peak vaginal wall blood flow, as graphically depicted in FIG. 2. Intravenous administration of 0.1 and 0.2 mg/kg apomorphine caused a statistically significant increase in nerve stimulation-induced peak vaginal wall blood flow compared to that observed before apomorphine administration (FIG. 2).

Apomorphine at concentration of 0.4 mg/kg produced an adverse effect on nerve stimulation-induced increase in vaginal wall blood flow.

3. Effect of apomorphine on systemic arterial pressure.

Figure 3:
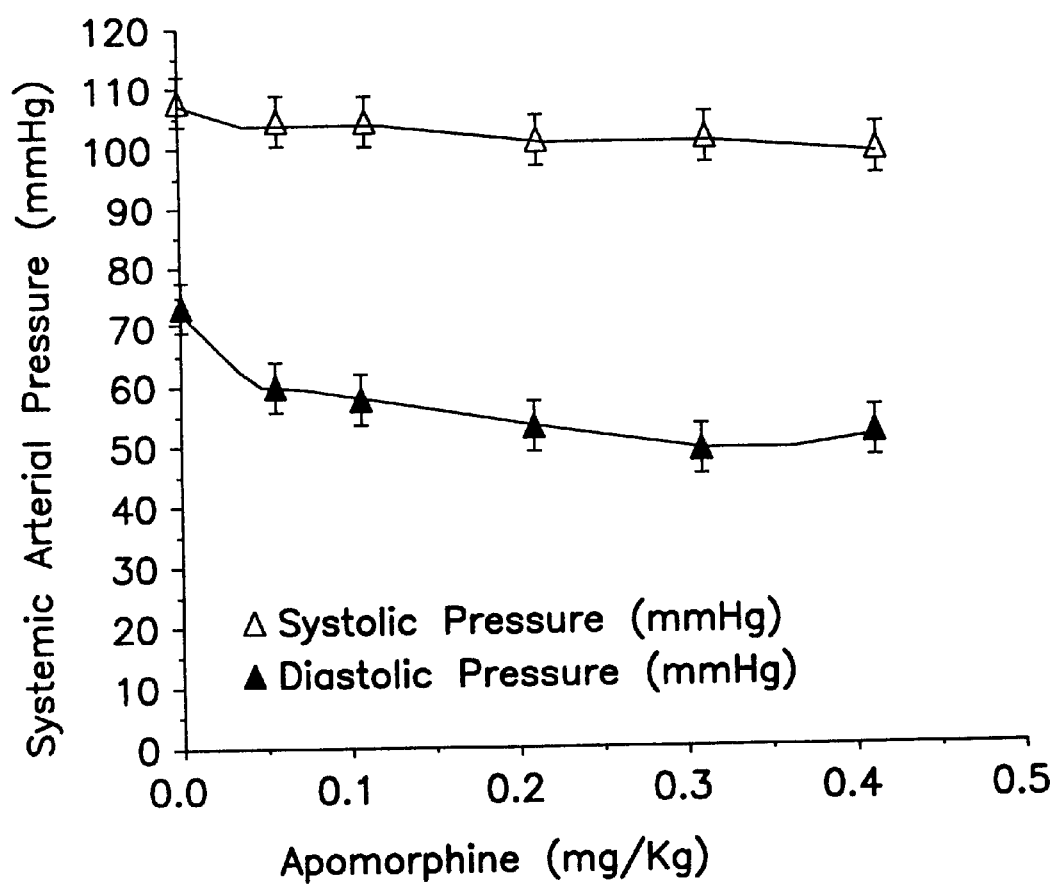
FIG. 3 is a graph depicting the effect of intravenous apomorphine on female rabbit systemic (diastolic and systolic) arterial pressure.

The effect of increasing doses of apomorphine on diastolic arterial pressure is shown in FIG. 3. Intravenous administration of apomorphine caused a concentration dependent moderate decrease in diastolic arterial pressure while having minimal effect on systolic arterial pressure.

Conclusion

Intravenous administration of apomorphine at a concentration of 0.1 mg/kg, 0.2 mg/kg and 0.3 mg/kg caused a significant increase in nerve stimulation-induced peak clitoral intracavernosal blood flow. Intravenous administration of apomorphine at a concentration of 0.1 mg/kg and 0.2 mg/kg caused a significant increase in vaginal wall blood flow. The main side effect of intravenous administration of apomorphine noted was a moderate decrease in diastolic blood pressure. A dose of about 0.1 mg/kg was judged optimal.

Studies with this female rabbit model showed that the hemodynamic mechanisms of clitoral erection and vaginal engorgement depend on the relaxation of clitoral cavernosal and vaginal wall smooth muscle. It is also known that in the human female, vasocongestion of the vagina entails lubrication of the vagina and swelling of the external genitalia during sexual excitation. Thus, the enhancement of clitoral blood flow by apomorphine in the female rabbit was judged indicative of improving clitoral erection, and the enhancement of vaginal blood flow by apomorphine was judged indicative of increasing vaginal lubrication and augmenting vaginal engorgement in human females.

It is known that dosage ranges with apomorphine hydrochloride are species dependent. In humans, the effective dosage compared to animals is about 1/10. Thus, an optimum dose of about 0.1 mg/kg given intravenously, based on the female rabbit study would correlate to an effective dose of about 0.01 mg/kg in a human female. Since sublingual administration of apomorphine is known to provide about 13% bioavailability compared to subcutaneous administered apomorphine, a dosage of about 76 micrograms/kg or about 5.3 mg tablet for a 70 kg weight woman produces a significant sexual readiness (clitoral erectogenesis and vaginal engorgement on sexual stimulation). Thus, a dosage range of about 2 to about 12 mg, preferably about 2 to about 8 mg., more preferably about 4 to about 6 mg. is sufficient for producing sexual readiness in women without inducing substantial nausea.

The foregoing discussion and the reported studies are intended as illustrative of the present invention and are not to be taken as limiting. Still other variants within the spirit and scope of this invention are possible and will readily present themselves to those skilled in the art.

We claim:

1. A method of ameliorating sexual dysfunction in a human female which comprises administering to said human female apomorphine in an amount sufficient to increase intraclitoral blood flow and vaginal wall blood flow on stimulation of said female but less than the amount that induces substantial nausea.

2. The method in accordance with claim 1 wherein the apomorphine is administered in a sublingual dosage form containing about 2 milligrams to about 12 milligrams of apomorphine.

3. The method in accordance with claim 1 wherein the amount of apomorphine administered is in the range of about 25 to about 80 micrograms per kilogram of body weight.

4. The method in accordance with claim 1 wherein the apomorphine is administered as the hydrochloride salt.

5. The method in accordance with claim 1 wherein the apomorphine is administered together with a β-cyclodextrin.

6. The method in accordance with claim 1 wherein the β-cyclodextrin is hydroxypropyl-β-cyclodextrin.

7. A method of stimulating dopamine receptors in the mid-brain region of a human female to cause clitoral erectogenesis and vaginal engorgement which comprises administering to the human female apomorphine about 25 to about 80 micrograms of apomorphine per kilogram of body weight and at a rate so as to maintain a plasma concentration of apomorphine of no more than about 5.5 nanograms per milliliter during sexual activity.

8. The method in accordance with claim 7 wherein the plasma concentration of apomorphine is maintained in the range of about 0.3 to about 4 nanograms per milliliter during sexual activity.

9. The method in accordance with claim 7 wherein the plasma concentration of apomorphine is maintained in the range of about 1 to about 2 nanograms per milliliter during sexual activity.

10. A method of ameliorating sexual dysfunction in a human female which comprises administering to said human female apomorphine in an amount sufficient to stimulation induce clitoral erectogenesis and vaginal engorgement and to maintain a plasma concentration of apomorphine at a level of no more than about 5.5 nanograms per milliliter.

11. The method in accordance with claim 10 wherein the plasma concentration of apomorphine is maintained at a level of about 0.3 to about 4 nanograms per milliliter.

12. The method in accordance with claim 10 wherein the plasma concentration of apomorphine is maintained at a level of about 1 to about 2 nanograms per milliliter.

13. The method in accordance with claim 10 wherein the amount of apomorphine administered is in the range of about 2 milligrams to about 12 milligrams.

14. The method in accordance with claim 10 wherein the amount of apomorphine administered is in the range of about 25 to about 80 micrograms per kilogram of body weight.

15. The method in accordance with claim 10 wherein apomorphine is administered as the hydrochloride salt.

16. The method in accordance with claim 1 wherein the administration is effected by a transdermal patch.

17. The method in accordance with claim 1 wherein the administration is effected by the application of a cream to the clitoral region of the patient.

18. The method in accordance with claim 1 wherein the administration is effected by a buccal patch.

* * * * *